US010342923B2

(12) United States Patent
Henrich et al.

(10) Patent No.: US 10,342,923 B2
(45) Date of Patent: Jul. 9, 2019

(54) CONTROL APPARATUS AND METHOD FOR CONTROLLING A MEDICAL SYSTEM, A PORTABLE DEVICE, AN ARRANGEMENT, AND A COMPUTER PROGRAM PRODUCT

(71) Applicant: Roche Diabetes Care, Inc., Indianapolis, IN (US)

(72) Inventors: Annika Henrich, Basel (CH); Til Rendschmidt, Wiesbaden (DE); Markus Graf, Worms (DE); Tobias Loerracher, Mannheim (DE); Simon Wetzel, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 15/846,334

(22) Filed: Dec. 19, 2017

(65) Prior Publication Data
US 2018/0104412 A1    Apr. 19, 2018

Related U.S. Application Data

(63) Continuation of application No. PCT/EP2016/064056, filed on Jun. 17, 2016.

(30) Foreign Application Priority Data

Jun. 19, 2015  (EP) .................................... 15172944

(51) Int. Cl.
*A61M 5/172*    (2006.01)
*G16H 40/63*    (2018.01)
(Continued)

(52) U.S. Cl.
CPC ...... *A61M 5/1723* (2013.01); *A61M 5/14244* (2013.01); *A61M 5/172* (2013.01);
(Continued)

(58) Field of Classification Search
CPC ............ A61M 5/1723; A61M 5/14244; A61M 5/172; A61M 2205/18; A61M 2205/3523;
(Continued)

(56) References Cited

U.S. PATENT DOCUMENTS 9,787,756 B2 * 10/2017 Gold ................... H04M 1/7253
2007/0276270 A1   11/2007 Tran
2014/0206954 A1    7/2014 Yuen

FOREIGN PATENT DOCUMENTS

EP       2 881 875 A2    6/2015
WO    WO 2009/151535 A1   12/2009

OTHER PUBLICATIONS

International Application PCT/EP2016/064056 International Search Report and Wrttten Opinion dated Oct. 5, 2016.

* cited by examiner

*Primary Examiner* — Lee Nguyen
(74) *Attorney, Agent, or Firm* — Woodard, Embardt, Henry, Reeves & Wagner, LLP

(57) ABSTRACT

The present disclosure relates to a control system for controlling a medical system. The control system comprising: a portable device, a transmitter placed in a location of a local use environment of the portable device, and a data handling system comprising a detection module, a data interface, and a device controller functionally connected to the detection module and the data interface. The data handling system is configured to detect local vicinity of the portable device to the at least one transmitter by the detection module, receive input data from the at least one transmitter via the data interface, generate device control data for a medical device, comprising processing of the input data, and transmitting the device control data to a control device. Furthermore, a portable device, a method for controlling a medical system,
(Continued)

Figure 1:
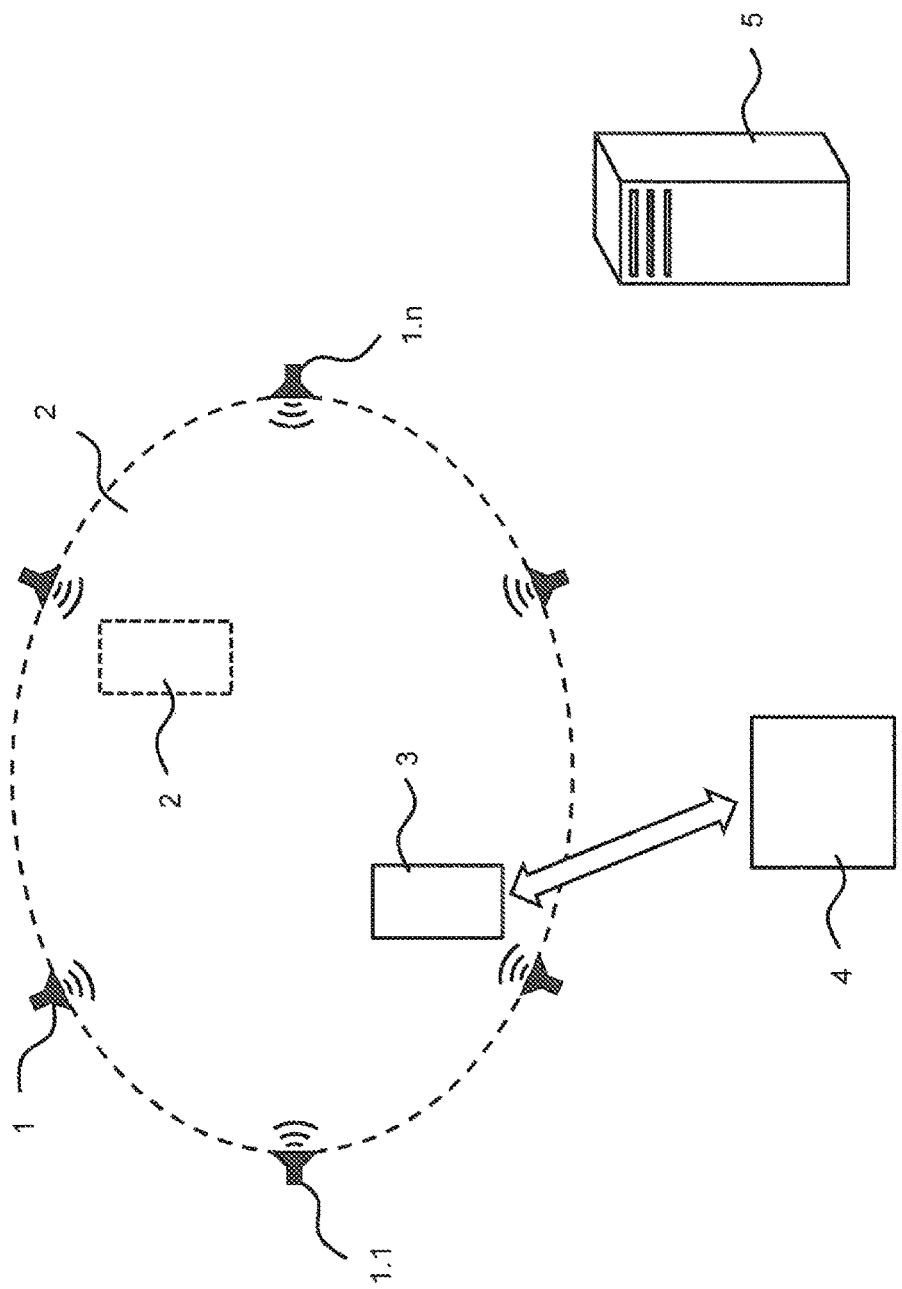

and a computer program product for controlling a medical system by a control system are disclosed.

19 Claims, 3 Drawing Sheets

(51) Int. Cl.
*A61M 5/142* (2006.01)
*G16H 20/17* (2018.01)
*G06F 19/00* (2018.01)

(52) U.S. Cl.
CPC .............. *G16H 20/17* (2018.01); *G16H 40/63* (2018.01); *A61M 2205/18* (2013.01); *A61M 2205/3523* (2013.01); *A61M 2205/3553* (2013.01); *A61M 2205/3561* (2013.01); *A61M 2205/3584* (2013.01); *A61M 2205/3592* (2013.01); *A61M 2205/581* (2013.01); *A61M 2205/583* (2013.01); *A61M 2205/6018* (2013.01); *A61M 2205/6054* (2013.01); *A61M 2205/6072* (2013.01); *A61M 2209/01* (2013.01); *A61M 2230/201* (2013.01); *A61M 2230/63* (2013.01)

(58) Field of Classification Search
CPC .. A61M 2205/3553; A61M 2205/3561; A61M 2205/3584; A61M 2205/3592; A61M 2205/581; A61M 2205/583; A61M 2205/6018; A61M 2205/6054; A61M 2205/6072; A61M 2209/01; A61M 2230/201; A61M 2230/63; G16H 20/17; G16H 40/63; G06F 19/00
USPC ................................................ 455/41.2–41.3
See application file for complete search history.

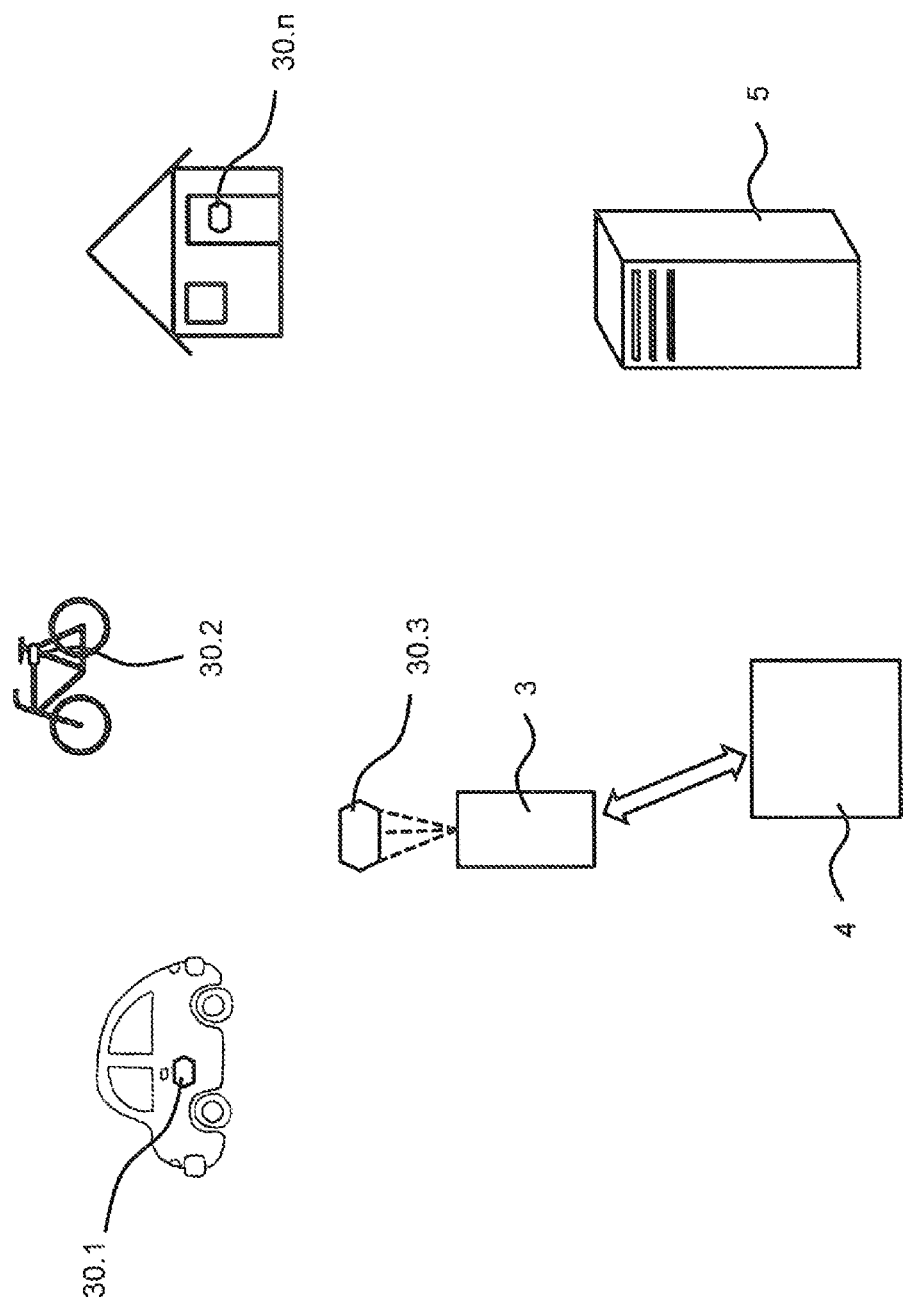

CONTROL APPARATUS AND METHOD FOR CONTROLLING A MEDICAL SYSTEM, A PORTABLE DEVICE, AN ARRANGEMENT, AND A COMPUTER PROGRAM PRODUCT

CROSS-REFERENCE TO RELATED APPLICATION

This application is a continuation of International Application No. PCT/EP2016/064056, filed Jun. 17, 2016, which claims the benefit of EP Application 15172944.9, filed Jun. 19, 2015, the entire disclosures of which are hereby incorporated by reference.

The invention relates to a control apparatus and method for controlling a medical system, a portable device, an arrangement, and a computer program product.

BACKGROUND

Such control system or apparatus and method provide for controlling operation of a medical system provided with device. For example, depending on an actual or present use situation of the medical device control data are generated and submitted to the medical device which in turn is operated according to the device control data. In a known medical system, a present use situation may be detected by one or more sensors. From sensor signals provided the one or more sensors the device control data may be derived by processing the sensor data representing the sensor signals.

EP 2 190 503 B1 discloses a wearable infusion pump system that includes an activity sensor for monitoring a user's activity while pump system is carried or otherwise worn by the user. The activity sensor detects the user's movement characteristics or the user's physiological parameters, which may be indicative of physical exercise or the like. Employing such a sensor allows to detect the activity level and to adjust a medicine dispensing regimen to the needs of the user accordingly.

U.S. Pat. No. 7,879,026 B2 describes an infusion pump system that incorporates an accelerometer or other motion sensor to detect the user's activity level. If the user's activity lever indicates that he or she is exercising or otherwise at an elevated level, the infusion pump device can be configured to automatically adjust the dispensation rate of a medicine such as insulin. Accordingly, an insulin delivery rate can be corrected to account for a user's activity level (e.g. an elevated activity level during exercise or the like) without having to rely on the user's instruction to change the delivery rate.

The system described in EP 1 255 578 B1 includes a measuring device for detecting values which are to be correlated with blood glucose levels, a controlling means which comprises a controller to process the measured values according to a control algorithm and a hormone dosing unit to administer a hormone dose. Additionally, the degree of physical activity of the diabetic is taken into consideration by a pilot control device having an activity measuring unit for the sensory detection of the degree of physical activity of the patient. With regard to the differentiated detection of resting states of the patient such as lying, sitting, standing, the pilot control device has a position sensor and in particular a mercury switch or spirit level. In order to detect states of movement the pilot control device has a movement sensor, such as a pedometer. For indirect detection the pilot control device can further include sensors for detecting body parameters of the patient such as heart rate, body temperature or skin conductivity.

U.S. Pat. No. 8,601,005 B2 discloses a portable device that accesses a food database over the internet. The portable device detects its location using GPS coordinates to detect its location. Based on the detected location, the portable device queries the food database, and the food database returns a list of menu items for that particular location. For example, if the first food source location is a fast food restaurant, the processor via the food database refines the list of available food items based on that location. If the portable device is located at the second food source location, then the menu of items would be based on the items available at that location. Manual entry of contextual data/health event (illness, sport. etc.) to automatically recommend bolus adjustment/correction (after use confirmation) does already exist (e.g., EP 2 627 251 B1).

SUMMARY

It is an object to provide improved technologies for controlling a medical system provided with a medical device to be operated. Specifically, operation of the medical system depending on different use situations shall be improved.

According to the present disclosure a control apparatus and a method for controlling a medical system according to claims 1 and 12, respectively, are provided. Claim 9 refers to a portable device. Further, an arrangement which comprises a medical device and a control apparatus according to claim 10 is provided. Also, a computer program product according to claim 15 is provided. Further developments are disclosed in dependent claims.

According to an aspect, a control apparatus for providing control data in a medical system is provided. The control apparatus comprises a portable device, and a plurality of context data carriers. The context data carriers comprise a first context data carrier placed in a first location of a use environment of the portable device. Further, the control apparatus comprises a data handling system provided in the portable device, the data handling system having a data input interface, and a device controller functionally connected to the data input interface. The data handling system is configured to receive, through the data input interface, first local context data from the first context data carrier, the first local context data being indicative of at least one of location, patient identity, patient activity, and time. The data handling system is further configured to generate, in response to receiving the first local context data, context dependent device control data by the device controller, comprising processing or analyzing of the first local context data and generating the first context dependent device control data in dependence on electronic context information derived from the processing of the first local context data. Further, the data handling system is configured to output, through a data output interface of the portable device, output data indicative of the first context dependent device control data.

According to another aspect, a portable device is provided. The portable device comprises a data handling system provided with a data input interface, and a device controller functionally connected to the data input interface. The data handling system is configured to receive, through the data input interface, first local context data from the first context data carrier; generate, in response to receiving the first local context data, context dependent device control data by the device controller, comprising analyzing of the first local context data and generating the first context dependent device control data in dependence on context information derived from the analyzing of the first local context data; and output, through a data output interface of the portable device, output data indicative of the first context dependent device control data.

According to still another aspect, an arrangement is provided, the arrangement comprising a medical device and a control apparatus. The medical device is functionally connectable to the control apparatus for receiving context-dependent device control data from the control apparatus. The arrangement comprising the medical device and the control system may be provided as a portable system, e.g. a portable system to be worn on a body. As an alternative, the medical system may be a non-portable medical system combined with the control system comprising the portable device.

According to a further aspect, a method for controlling a medical system is provided. The method comprises providing a control apparatus, the control apparatus comprising a portable device, a plurality of context data carriers with a first context data carrier individually placed in a first location of a use environment of the portable device, and a data handling system provided in the portable device and comprising a data input interface, and a device controller functionally connected to the data input interface. Through the data input interface first local context data are received from the first context data carrier. In response to receiving the first local context data context dependent device control data are generated by the device controller, comprising analyzing of the first local context data and generating the first context dependent device control data in dependence on context information derived from the analyzing of the first local context data. Output data indicative of the first context dependent device control data are outputted through a data output interface of the portable device.

Further a computer program product is provided for controlling a medical system by a control apparatus comprising a portable device, a plurality of context data carriers provided with context data carrier placed in a first location of a use environment of the portable device, and a data handling system provided in the portable device and comprising a data input interface, and a device controller functionally connected to the data input interface, the computer program product comprising means recorded on an electronic data carrier for performing the method for controlling a medical system.

The local context data may be provided with encrypted local context data on the context data carrier.

The local context data may be indicative of at least one of location, patient identity, patient activity, and time. Location data may be indicative of a location where the context data carrier is placed. Patient activity data may indicate a level of physical activity. For example, the patient's level of activity will be different for working in the office on one side and for doing exercises in a gym on the other side. With regard to time, the context data may refer to different control data depending on the day time.

The term (local) context data as used here refers to data indicative of at least one of location, patient identity, patient activity, and time. The context data, for example, may be provided by text information. The term context dependent control data which may also be referred to as contextualized or contextual (control) data as used here refers to control data such as a control signal value which is assigned to or dependent on some context indicated by the context data. The context dependent control data may be contained in or directly derivable from the context data itself. For example, the text information (context data) may assign a signal value (context dependent control data) received from the local context data carrier to such context data carrier by providing data carrier identification, e.g. some alphanumeric code like "DC 1".

As an alternative of or in addition to having contained the context dependent control data in the local context data, the local context data may refer to a data assignment between context data and control data, e.g. a look-up table providing assignment between the local context data and the (context dependent) control data. Different context data may refer or point to different context dependent control data. For example, context data indicating different locations may be pointing at different context dependent control data, e.g. a first and a second bolus administration, the second bolus administration being different from the first one.

The context dependent control data may be configured to control a data output, e.g. outputting video and/or acoustic information through a display and a speaker, respectively. As an alternative or in addition, the context dependent control data may be configured to control operation of a functional element of a medical device provided in the medical system, such as an insulin pump or a sensor device. In such case, output of the output data through the data output interface of the portable device further comprises transmitting the context dependent control data to the medical device. In an embodiment, operation of a glucose sensor may be controlled by the context dependent control data. By the functional element of the medical device a medication may be administered.

The context dependent control data are generated in the portable device in response to receiving the context data for at least one of the context data carriers. The generation may be started and performed without requesting or responding to any (additional) user input.

The data handling system may be further configured to receive the local context data by at least one of the following: reading local context data from a passive local context data carrier by a contactless data reader of the portable device; and receiving, by a receiver of the portable device, local context data transmitted by a transmitter of an active context data carrier. The wording active storage element as used here refers to a data storage element provided with a transmitter for transmitting the data. Contrary, with regard to the transmitter, the passive data storage element is void. The data reader, for example, may comprise a scanner configured to scan the data matrix and/or an RFID reader. An arrangement of transmitters may be provided by a plurality of active context data carriers. For example, the active context data carriers may be provided beacon technology, e.g., based on the Bluetooth technology.

The passive local context data carrier may comprise at least one of a data matrix such as a one-dimensional barcode and/or a two-dimensional barcode, and an electronic data storage element such as an RFID transponder. The electronic data storage element is readable by the contactless reader for downloading the local context data to the portable device, but the electronic data storage element is free of a data transmitter. The data matrix may be printed on a support element, e.g. a label, a tag, or a marker. The data transmission between the transmitter arrangement and the data handling system may be configured for contactless data communication within a local range of communication. The local range of communication may be limited to contactless data communication over a distance of not more than about 10 m. As an alternative, the local range of communication may be limited to contactless data communication over a distance of not more than about 5 m, in a further alternative to a distance of not more than about 1 m. The transmitter may be provided in a transceiver. The transceiver is implementing a transmitter and a receiver configured for transmitting and receiving data, respectively. The arrangement may be provided as a transceiver arrangement.

For at least one of the active context data carrier and the passive context data carrier the local context data may be provided with the data carrier at the time a placing the data carrier in the use environment. The local context data may be provided with persistent local context data. With regard to the electronic data stored in a data storage element, the persistent data may be provided by electronic data which cannot be overwritten.

The active context data carrier and/or the passive context data carrier may be free of any sensor device, and may be also not connected to a sensor device.

The transmitter of the context data carrier and the receiver of the portable device may be configured for contactless data transmission by a transmission technology selected from the following group: near field data communication, and Bluetooth communication.

The portable device may comprise a detection module functionally connected to the device controller, the data handling system further configured to detect local vicinity of the portable device to the first context data carrier. In response to the detection of local vicinity of the portable device to the at least one context data carrier, the controller device may generate a detection signal. Following, the local context data may be received in the portable device.

The first context dependent device control data may be configured to control at least one process of operation of a medical device selected from the following group of processes of operation: video data output, audio data output, outputting a warning signal, controlling pump operation, and amending at least one of medication plan, a bolus administration, a target range of measurement such as glucose values, a device setting of a medical device such as an insulin pump or a glucose measurement device, a threshold value for measurement values such as glucose values, an insulin profile, and a time block defining a time period. The time block may be defining a time period of validity for one or more of the other data such as the medication plan, the bolus administration, the target range of measurement such as glucose values, the device setting of a medical device such as an insulin pump or a glucose measurement device, the threshold value for measurement values such as glucose values, and/or the insulin profile.

The portable device may be selected from the following group of portable devices: mobile phone, tablet computer, laptop computer, portable medical device, portable medical measurement device, and smart watch.

The plurality of context data carriers may comprise a second context data carrier placed in a second location of the use environment of the portable device which is different from the first location, the second local context data carrier providing second context data which are different from the first local context data.

With regard to the active context data carrier, detection of the local vicinity of the portable device to the at least transmitter may include unidirectional data transmission and/or bidirectional data transmission between the at least one transmitter and the portable device. In an alternative the detection module detects local vicinity to the at least one transmitter by only receiving input data from the at least one transmitter. Such receiving of input data indicates local vicinity to the at least one transmitter. With regard to such embodiments, data transmission is implemented by actively sending the data by a sender and receiving such data by a receiver.

The transmitter arrangement may provide a local location reference system. The local reference system may be configured for determining a local position of the portable device when the portable device is in local proximity to at least one transmitter of the transmitter arrangement. Determining the local position of the portable device may include determining position data indicating the position of the portable device within the local reference system. As an alternative, determining the local position of the portable device may include determining presence off the portable device within the local reference system, without determining actual position data. For example, it may just be determined that the portable device is in the vicinity of one or more transmitters. Determining the local position of the portable device may be done by the data handling system provided in the portable device.

Zones of transmission of transmitters of the transmitter arrangement defining an individual coverage of the transmitter may be partially overlapping. There may be a fully covered three dimensional coverage zone of the transmitter arrangement. As an alternative, the transmitter arrangement may provide for a group of individual local transmitter zones separated from each other, such local zones being defined by the individual coverage of the locally placed transmitter.

The portable device and the medical device may be provided by separated devices or, as an alternative, as a single system. Both devices may be provided in a single housing or in a plurality of sub-housings connected. If the portable device and the medical device are provided as a combined device such combined device may be provided as a single portable device. The components of the combined device may de-connectable.

The control device which may be provided with a processor and a data storage device in the medical device may be connected to one or more functional components of the medical device and may be configured to generate control signals for a single functional component or a plurality of functional components, such as data interfaces and/or output devices for outputting video and/or audio signals. For example, the control device may be configured to control operation of a sensor device and/or a pump device provided in the medical device.

The aspects of the present disclosure are applicable to different setups of medical systems. For instance the medical system may include a controller and an insulin delivery system, such as a durable or a patch pump, or a controller and a glucose monitor, such as a BG meter or a continuous glucose monitoring sensor. The controller may be provided in the portable device. As another example, the technology may also be applied to integrated or closed-loop systems including an insulin delivery and a monitoring device.

In an embodiment, as an article a set comprising a portable device and a plurality of transmitters may be provided. Such article will give a user the opportunity to individually create a local arrangement of transmitters which can be adjusted to different user situations by user defined placing of the transmitters.

A local reference grid of transmitters may be provided by the transmitter arrangement. A fixed reference system provided by transmitters in fixed locations may be provided.

Data transmission between the transmitter arrangement and the data processing device may be configured for contactless data communication within a local range of communication. Near field communication (NFC) may be used for data transmission. The components of the control system may be restricted to local data communication only. As an alternative RFID technology may be used for data exchange. Also, as an alternative or in addition, beacon technology, e.g. using Bluetooth transmitter, may be provided. In another alternative, data exchange with equipment of a WLAN (wireless local area network) may be used for determining the local position of the portable device. For example, a method based on the process of triangulation known as such may be applied.

The portable device may be selected from the following group of portable devices: mobile phone, tablet computer, laptop computer, portable medical device, portable medical measurement device, and a smart watch. The portable device may be configured with a software program being downloaded from the internet, for example, in form of a so-called App. Also the remote control by the portable device may be provided by a program pre-installed/updated, wherein the remote control may be configured to communicate with components of the medical device only. With regard to the arrangement comprising a medical device and a control apparatus and the method for controlling a medical system, the features outlined above may also apply. In the arrangement the medical device may be selected from the following group of medical devices: blood glucose meter, insulin pump, continuous glucose monitoring system, and insulin pen.

Regarding the arrangement, the medical device may be placed within the local reference system provided by the transmitter arrangement.

With regard to the method, the step of providing the control system may comprise loading a software application into a memory of the portable device and running the software application on the portable device. The software application, for example, may be downloaded via the internet. One or more web applications may be part of the implementation and/or the running process of the software application.

The method for controlling the medical system may further comprise placing the at least one transmitter in a user-defined location of the local use environment of the portable device. The location of one or more transmitters may be changed (relocation), thereby, changing the transmitter arrangement to another user-defined configuration.

Following, alternative aspects are disclosed. According to an alternative, a control system for controlling a medical system is provided. The control system comprises a portable device, and a transmitter arrangement. The transmitter arrangement is provided with at least one transmitter individually placed in a location of a local use environment of the portable device. Further, the control system comprises a data handling system provided in the portable device, the data handling system comprising a detection module, a data interface, and a device controller functionally connected to the detection module and the data interface. The data handling system which may also be referred to as data processing system is configured to detect local vicinity of the portable device to the at least one transmitter by the detection module, receive input data from the at least one transmitter via the data interface, generate device control data for a medical device by the device controller, comprising processing of the input data, and transmitting the device control data to a control device of the medical device.

A portable device may be provided. The portable device is comprising a data handling system provided with a detection module, a data interface, and a device controller functionally connected to the detection module and the data interface, wherein the data handling system is configured to detect local vicinity of the portable device to at least one transmitter by the detection module; receive input data from the at least one transmitter via the data interface; generate device control data for a medical device by the device controller, comprising processing of the input data; and transmitting the device control data to a control device of the medical device. The portable device is configured to be used with the control system.

An arrangement may be provided, the arrangement comprising a medical device and a control system, wherein the medical device is functionally connectable to the control system for receiving device control data from the control system. The arrangement comprising the medical device and the control system may be provided as a portable system, e.g. a portable system to be worn on a body. As an alternative, the medical system may be a non-portable medical system combined with the control system comprising the portable device.

As an alternative, a method for controlling a medical system may be provided. The method comprises providing a control system, the control system comprising a portable device, a transmitter arrangement provided with at least one transmitter individually placed in a location of a local use environment of the portable device, and a data handling system provided in the portable device and comprising a detection module, a data interface, and a device controller functionally connected to the detection module and the data interface. Local vicinity of the portable device to the at least one transmitter is detected by the detection module. Further, input data are received by the data handling system from the at least one transmitter via the data interface. Device control data for a medical device are generated by the device controller, comprising processing of the input data. The device control data are transmitted to the medical device via the data interface, and the medical device is controlled or operated according to the device control data.

Further a computer program product may be provided for controlling a medical system by a control system comprising a portable device, a transmitter arrangement provided with at least one transmitter individually placed in a location of a local use environment of the portable device, and a data handling system provided in the portable device and comprising a detection module, a data interface, and a device controller functionally connected to the detection module and the data interface, the computer program product comprising means recorded on an electronic data carrier for performing the method for controlling a medical system.

Detection of the local vicinity of the portable device to the at least transmitter may include unidirectional data transmission and/or bidirectional data transmission between the at least one transmitter and the portable device. In an alternative the detection module detects local vicinity to the at least one transmitter by only receiving input data from the at least one transmitter. Such receiving of input data indicates local vicinity to the at least one transmitter.

The transmitter arrangement may provide a local location reference system. The local reference system may be configured for determining a local position of the portable device when the portable device is in local proximity to at least one transmitter of the transmitter arrangement. Determining the local position of the portable device may include determining position data indicating the position of the portable device within the local reference system. As an alternative, determining the local position of the portable device may include determining presence off the portable device within the local reference system, without determining actual position data. For example, it may just be determined that the portable device is in the vicinity of one or more transmitters. Determining the local position of the portable device may be done by the data handling system provided in the portable device.

Zones of transmission of transmitters of the transmitter arrangement defining an individual coverage of the transmitter may be partially overlapping. There may be a fully covered three dimensional coverage zone of the transmitter arrangement. As an alternative, the transmitter arrangement may provide for a group of individual local transmitter zones separated from each other, such local zones being defined by the individual coverage of the locally placed transmitter.

The portable device and the medical device may be provided by separated devices or, as an alternative, as a single system. Both devices may be provided in a single housing or in a plurality of sub-housings connected. If the portable device and the medical device are provided as a combined device such combined device may be provided as a single portable device. The components of the combined device may de-connectable.

The control device which may be provided with a processor and a data storage device in the medical device may be connected to one or more functional components of the medical device and may be configured to generate control signals for a single functional component or a plurality of functional components, such as data interfaces and/or output devices for outputting video and/or audio signals. For example, the control device may be configured to control operation of a sensor device and/or a pump device provided in the medical device.

The aspects of the present disclosure are applicable to different setups of medical systems. For instance the medical system may include a controller and an insulin delivery system, such as a durable or a patch pump, or a controller and a glucose monitor, such as a BG meter or a continuous glucose monitoring sensor. The controller may be provided in the portable device. As another example, the technology may also be applied to integrated or closed-loop systems including an insulin delivery and a monitoring device.

As an article a set comprising a portable device and a plurality of transmitters may be provided. Such article will give a user the opportunity to individually create a local arrangement of transmitters which can be adjusted to different user situations by user defined placing of the transmitters.

A local reference grid of transmitters may be provided by the transmitter arrangement. The at least one transmitter may be in a fixed local position at least at a data exchange time when, by the detection module, local vicinity is detected and the input data are received via the data interface. A fixed reference system provided by transmitters in fixed locations may be provided.

With regard to the alternative, data transmission between the transmitter arrangement and the data processing device may be configured for contactless data communication within a local range of communication. Near field communication (NFC) may be used for data transmission. The components of the control system may be restricted to local data communication only. As an alternative RFID technology may be used for data exchange. Also, as an alternative or in addition, beacon technology, e.g. using Bluetooth transmitter, may be provided. In another alternative, data exchange with equipment of a WLAN (wireless local area network) may be used for determining the local position of the portable device. For example, a method based on the process of triangulation known as such may be applied.

The local range of communication may be limited to contactless data communication over a distance of not more than about 10 m. As an alternative, the local range of communication may be limited to contactless data communication over a distance of not more than about 5 m, in a further alternative to a distance of not more than about 1 m. The at least one transmitter may be provided in a transceiver. The transceiver is implementing a transmitter and a receiver configured for transmitting and receiving data, respectively. The arrangement may be provided as a transceiver arrangement.

The device control data may be configured to control at least one process of operation of the medical device selected from the following group of processes of operation: video data output, audio data output, outputting a warning signal, controlling pump operation, amending a medical therapy plan, and amending a medication plan.

The portable device may be selected from the following group of portable devices: mobile phone, tablet computer, laptop computer, portable medical device, portable medical measurement device, and a smart watch. The portable device may be configured with a software program being downloaded from the internet, for example, in form of a so-called App. Also the remote control by the portable device may be provided by a program pre-installed/updated, wherein the remote control may be configured to communicate with components of the medical device only.

At least one of the input data and the device control data may comprise contextualized data. The term contextualized data as used here may refer to a combination of a signal value combined with text information. For example, with regard to input data, the text information may assign a signal value received from a transmitter to such transmitter by providing a transmitter identification, e.g. some alphanumeric code like "TR 1". With regard to the device control data, the text information added to a control signal value may indicate the functional element which is to be controlled by the control signal value.

The input data and/or the device control data, comprising contextualized data or not, may be processed by the control device of the medical device in the course of processing medical data in the medical device. In the medical device medical data processing may include processing the input data and/or the device control data. For example, a frequency of performing medical data processing in the medical device, e.g. determining a blood glucose value from measurement data, may dependent on the input data and/or the device control data.

With regard to the arrangement comprising a medical device and a control system and the method for controlling a medical system, the features outlined above may also apply. In the arrangement the medical device may be selected from the following group of medical devices: blood glucose meter, insulin pump, continuous glucose monitoring system, and insulin pen. Regarding the arrangement, the medical device may be placed within the local reference system provided by the transmitter arrangement.

With regard to the method, the step of providing the control system may comprise loading a software application into a memory of the portable device and running the software application on the portable device. The software application, for example, may be downloaded via the internet. One or more web applications may be part of the implementation and/or the running process of the software application.

DESCRIPTION OF FURTHER EMBODIMENTS

Figure 2:
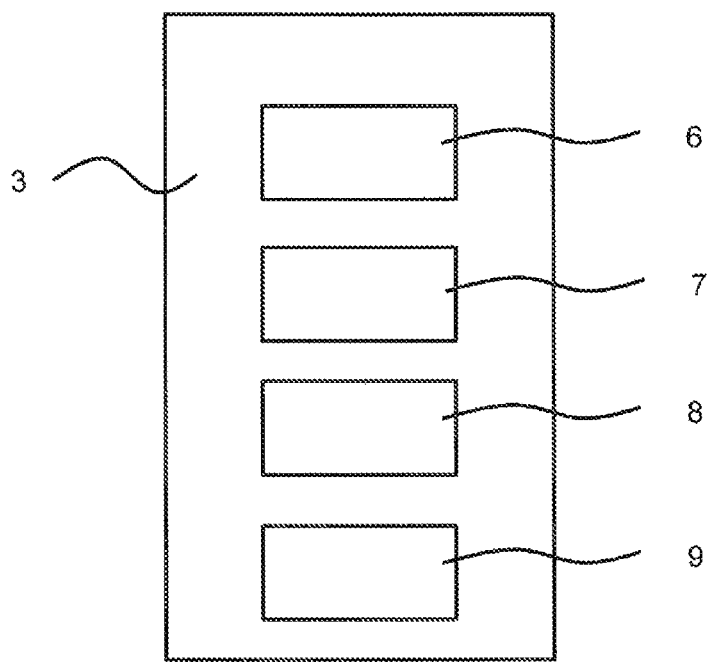

Following, embodiments, by way of example, are described with reference to figures. In the figures show:

FIG. 1 a schematic representation of a control system for controlling a medical system;

FIG. 2 a schematic representation of a portable device; and

FIG. 3 a schematic representation of an alternative control system for controlling a medical system.

FIG. 1 shows a schematic representation of a control system or apparatus for controlling a medical system. There is an arrangement 1 provided which comprises a plurality of active context data carriers 1.1, . . . , 1.$n$, the active context data carriers 1.1., . . . , 1.$n$ each provided locally with a data transmitter. The active context data carriers 1.1, . . . , 1.$n$ cover a local area 2, thereby, providing a fixed local reference system. A portable device 3 is provided which, for example, is a mobile phone or a tablet computer. The covered area 2 provides an area of use for the portable device 3.

As shown in FIG. 1, the portable device 3 is located in the vicinity of one of the active context data carriers 1.1, . . . , 1.$n$. Such vicinity is detected by the portable device 3. In response to the detection of the vicinity to one of the active context data carriers, context dependent device control data are generated in the portable device 3 and transmitted to a medical device 4. The medical device 4, for example, may implement a blood glucose meter or an insulin pump. In response to receiving the context dependent device control data from the portable device 3, the medical device 4 is operated according to the context dependent device control data.

As an alternative, the context dependent control data generated in the portable device may provide for controlling data output by the portable device, for example, outputting video and/or audio data through a display of the portable device 3 an a speaker of the portable device 3, respectively.

With regard to the FIG. 1, the arrangement may be provided as a transmitter arrangement. The active context data carriers 1.1, . . . , 1.$n$ may be provided as a plurality of transmitters. The arrangement of transmitters may cover the local area 2, thereby, providing a fixed local reference system. With regard to such alternative, as shown in FIG. 1, the portable device 3 is located in the vicinity of one of the transmitters from the plurality of transmitters. Such vicinity may be detected by the portable device 3. In response to the detection of the vicinity to one of the transmitters, device control data are generated in the portable device 3 and transmitted to a medical device 4. The medical device 4, for example, may implement a blood glucose meter or an insulin pump. In response to receiving the device control data from the portable device 3, the medical device 4 is operated according to the device control data.

With regard to the system shown in FIG. 1, there is a central server device 5 which may be connected to the portable device 3 and/or to the medical device 4 for data transmission, for example, via the internet. In an embodiment, the remote control function provided by the portable device 3 may be implemented on the portable device 3 by downloading a software application from the central server device 5 and running the software application on the portable device 3.

FIG. 2 shows a schematic representation of the portable device 3 in more detail. For providing the remote control to the medical device 4 in response to locating the portable 3 within the arrangement 1 of the active context data carrier 1.1, . . . , 1.$n$ which may be provided by transmitters, the portable device 3 is provided with a detection module 6, a data input interface 7 (or data interface), and a device controller 8 functionally connected to the detection module 6 and the data input interface 7. A data output interface 9 functionally connected to the device controller 8 is provided for outputting data. When the portable device 3, within the local area 2, is brought in local vicinity to the respective active context data carrier the detection module 6 is receiving local context data from at least one of the active context data carrier 1.1, . . . , 1.$n$.

In response to receiving input data such as the local context data from one or more of the active context data carrier 1.1, . . . , 1.$n$, context dependent device control data or device control data for the medical device 4 are generated by the device controller 8. In such process of generating context dependent device control data the local context data are processed in the portable device 3. The control data such as the context dependent device control data generated are transmitted to a control device of the medical device 4. Following, operation of the medical device 4 is controlled according to the context dependent device control data received from the portable device 3. The control data received may control any function of the medical device 4. One or more operation functions may be controlled by the device control data.

In an alternative embodiment, the context dependent control data generated in the portable device 3 in response to receiving the context data may be provided for controlling data output of the portable device 3 itself. Such data output control may be provided as an alternative or in addition to providing the context dependent control data to the medical device 4.

FIG. 3 shows a schematic representation of an alternative control system for controlling a medical system. There is a plurality of passive context data carriers 30.1, . . . , 30.$n$ located in different locations in the use environment of the portable device 3. Contrary to the active context data carriers 1.1, . . . , 1.$n$, the passive context data carriers 30.1, . . . , 30.$n$ are free of a data transmitter. Ruther, the context data provided by the respective passive context data carrier can (only) be read out from the data carrier by one or more technologies, but not actively transmitted by a data sender from the data carrier. The For example, one of the passive context data carriers 30.1, . . . , 30.$n$ may be provided in the car of the patient owning the portable device 3. Another one of the passive context data carriers 30.1, . . . , 30.$n$ may be provided in the apartment of the patient owning the portable device 3 or on the patient's bicycle.

In an alternative embodiment, the use environment of the portable device 3 may be provided with a combined arrangement of context data carriers comprising at least one active context data carrier and at least one passive context data carrier At least some of the passive context data carriers 30.1, . . . , 30.$n$ are providing different context data which can be read out by the portable device 3, for example, by a scanner or contactless reader provided with the portable device 3. With regard to the embodiment shown in FIG. 3, the portable device 3 not necessarily needs to comprise the detection module 6. In response to receiving the local context data from at least one of the passive context data carriers 30.1, . . . , 30.$n$, the context dependent control data are generated in the portable device 3.

The passive context data carriers 30.1, . . . , 30.$n$ may be "carrying" or providing the local context data by means of a data matrix such as a one-dimensional or a two-dimensional barcode and/or an electronic data storage element.

The context dependent control data may be directly contained in the local context data. In such case contextualized or contextual control data may be provided by the passive context data carriers 30.1, . . . , 30.n directly. Similarly, the active context data carrier 1.1, . . . , 1.n may provide contextualized or contextual data.

As an alternative or in addition, the local context data provided by the passive context data carriers 30.1, . . . , 30.n or the active context data carrier 1.1, . . . , 1.n may refer to a data assignment, e.g. a look-up table providing assignment between the local context data and the context dependent control data. Different context data may refer or point to different context dependent control data. For example, context data indicating different locations may be pointing at different context dependent control data, e.g. a first and a second bolus administration, the second bolus administration being different from the first one.

Today the person with diabetes has to manually adjust their therapy settings every time depending on, for example, location, time and activity. Thus, there is always a possibility that the wrong values are chosen. For example, an insulin pump/patch pump/cgm or another diabetes device which is used by people with diabetes (smartphones, smartwatches) as a medical device may work together with the control system or apparatus to enable and provide new opportunities in the therapy.

The location data may be used to initiate a notification to the user/patient about carrying some sugar containing food when leaving the house. The transmitter or context data carriers arrangement provides a local reference or use system located in the house of the user/patient. A context data carrier such as a transmitter may be located close to the door ("door or entrance transmitter"). When the portable device gets into the vicinity of such transmitter, location information provided by the context data carrier or transmitter is processed and context dependent control data such as a recommendation are outputted. As an alternative or in addition, a therapy plan implemented and/or outputted to the user (patient) may be amended in response to receiving the local context data from the door transmitter.

An alternative example can include a context data carrier which may be an active or a passive context data carrier, e.g. a transmitter, placed in the car (location data=car) and as context or contextual data ranges of the warning limits, e.g. with regard to a glucose level, may be adjusted to comply with what is considered safe for driving. An alternative case includes such context data carriers such as transmitters on sport equipment of the user, which signifies a higher activity level and may trigger a lower basal rate. Sensors may e.g. be attached to the sport shoe and the shirt. Identifying both in close proximity may allow for an additional plausibility check. Also, through the context data carriers, therapy data may be accessible to others depending on the location data and/or context data like the activity level. The adjustment may further include safety checks via additional data from the controller (GPS—Global Positioning System, date, time), activity sensors and so on. Detection of vicinity to the transmitter(s) in the car may be used for adjusting appropriate diabetes value limits (bG>120 mg/dl or 6.7 mmol/l) during a drive. Similarly, one or more passive context data carrier may be provided in the car. A notification would appear if the diabetic passes the range for secure driving. In addition every two hours the blood glucose level should be checked. Therefore the time is used to start a timer at the beginning of the drive. After two hours the diabetic get notified to check his/her blood glucose. If the diabetic is not driving anymore, the values will be set to default and the timer stops.

In another alternative, if the system provides the ability to configure different basal rate profiles, for example one for work days and one for the weekends, location information (context data) indicating the presence of the portable device (and the medical device) at home or at the working place may be used to activate automatically the right profile based on the weekdays. Independent context data carrier arrangements or transmitter arrangements at home and at the working place will be used for locating the position of the portable device.

With regard to physical activity of the user or patient, the location information provided with the context data may be used to automatically adjust warning limits for blood glucose levels. Warning limits which are to be set or re-set in the portable device 3 by the context dependent control data may be derived from the context data read directly or may be derived from a look-up table to which the context data point. If the diabetic blood glucose level is getting low, the patient would be notified and the right amount of carbohydrates are suggested to continue the workout. In addition, if the system provides the ability to configure different basal rate profiles, e.g. for a sport profile, the profiles can be activated automatically with adjusted basal rates by the context dependent control data. For example, a context data carrier such as transmitters may be provided on a bicycle and/or in a place providing storage place for the bicycle.

As an example, the active context data carriers 1.1, . . . , 1.n or the transmitters may be provided by beacons. Configurable Bluetooth beacons (cp. iBeacon) may be used as context data carrier configured to activate different kind of settings by the context dependent control data (medical device control). As an example, a Bluetooth beacon may be attached to the sport bag. If the diabetic is about to do sport, the signals of the beacon is used to activate the diabetics predefined sport basal profile. Another possibility could be use of Bluetooth beacons in a restaurant, where the right amount of carbohydrates are provided through a transmitter attached to a dinner tray or plate.

The location data which may be provided by the local context data may be used to provide the context dependent control data indication information in the native language of the inhabitants of the visited country such as "Help, I'm diabetic!" or "Where is the next pharmacy?" or "Call an ambulance!". For such purpose, one or more context data carriers which may be provided with a transmitter may be located at a customer booth.

In an alternative setup the context data carriers such as transmitters may form a fixed reference system or a grid, in which the medical device such as a pump/blood glucose sensor/controller system moves. The portable device 3 may detect individually placed transmitters, when it enters into close proximity of one of the transmitter. Based on the proximity to the transmitter and the context data received, the system can provide conclusions on the user's situation and may adjust the therapy accordingly. Such therapy adjustments may comprise for example a change in the basal rate, the warnings (alarm settings or blood glucose warning limits) or the bolus.

The different aspects of the technology disclosed are applicable to different setups of medical systems. For instance, the system may include a controller and an insulin delivery system (medical device), such a durable or a patch pump, or a controller and a glucose monitor, such as a BG meter or a continuous glucose monitoring sensor. It may also be applicable to integrated or closed-loop systems including an insulin delivery and a monitoring device.

When the medical system and in particular the controller (portable device) moves in the fixed reference systems of context data carriers such as the transmitters, the therapy adjustment depends on the location that is transmitted to the controller and the contextual information linked to that localization data.

The active context data carriers or the transmitters may be distributed in an individualized manner in different locations depending on habits of the patient. The context data may be provided directly by the transmitter (information stored on the context data carrier e.g. transmitter attached to a plate in restaurant with information on carbs), via a look-up table stored on the controller for matching the location with the contextual data or a remote database which can be connected via a network.

Following, with regard to the passive context data carrier further aspects are provided. Reference is made to an embodiment in the field of diabetes management. A barcode provided on the context data carrier may be used for changing user settings in relation to his diabetes management. The barcode may contain an indicating code (id) for referring to a specific preset profile or contains data for creating a new setting. Two types of barcodes may be applied: one dimensional and two dimensional.

With regard to the context dependent control data, for both types different usages may be provided: identifying a preset setting, and creating a new setting. The individual settings which may be identifiable or rather creatable may refer to at least one of insulin profile; target range of BG value for a specific time; and threshold (upper and lower limit) of BG value for a specific time.

For the context related settings time blocks may be assigned. A time block as referred here is a timespan with start time and end time indicating a listed above treatment setting with corresponding value.

In case of a one-dimensional barcode the barcode may be defined with standard EAN-13, which is a 13 digit barcode where one digit is a checksum. The number of usable digits is 12. In some alternative, the first two digits indicate, what is to be set or created: 00—insulin profile; 01—meal bolus; 02—target range of BG value for a specific time; and 03—threshold (upper and lower limit) of BG value for a specific time.

The next four digits may represent a timespan in which the setting is valid or an indication for loading a preset data record. If the four digits are 9999 it is indicating a preset record. If the digits are 9898, a not time relevant change is indicated. Otherwise the digits indicate a start and end time, each using two digits and a resolution of 15 minutes. These two digits begin with 00, which represents 00:00 h. From this point these are increasing by one representing an addition of 15 minutes to the real time. (e.g. 01 representing 00:15 h, 6 representing 01:30 h). This values count up to 96, which represents 24:00 h. The first value has to be less than the second one.

The next six digits may represent the value or values for creating the setting or contain the id, which is comparable on the scanner.

In case of a two-dimensional barcode (QR Code) the same encoding as for the one-dimensional Barcodes can be used. The encoding is defined in ISO/IEC 18004:2006 and shall use a high fault tolerance. An alternative option is to encode the data as an xml string. For the indication or creation of setting tags and attributes are used.

The one- or the two-dimensional barcode provided by the context data carrier may be scanned by a barcode reader or scanner integrated with or connect to the portable device 3. The Scanner for the barcode is using IR (infra read), laser or camera for reading the barcode. It translates the given code or xml into usable data or determines the preset setting based on an id. In usage this can be a handheld with camera. The user may open a software application running on the portable device 3 and click a button to activate the camera and keep it over the barcode. In response to reading the context data, the context dependent control data (settings) are generated.

Further, further alternative embodiments are described. There are persons with diabetes. These have to set values for the above mentioned usages over the day. At different times over the day the values (control data) can vary depending on the different body behavior or activity.

In a first use case the person with diabetes is working in an office. On his desk he fixes a first context data carrier provided with a first barcode for indicating an insulin profile for little movement. After work the person goes to his car where he attaches a second context data carrier provided a second barcode on the steering wheel. The second barcode provides for different context data indicating, for example, another threshold for warning the person early if he gets low with regard to the individual glucose level. In addition, in the car a third context data carrier provided with a third barcode may be placed, the third barcode may indicate another insulin profile which keeps the person awake. In the evening the person scans a fourth barcode provided on a fourth context data carrier for his sleep, where he has another target range, warning limit and insulin profile.

In a second use case the person with diabetes is going into a gym. For sport he needs specific settings. For the fast configuration he is scanning barcode of context data carriers attached to the entrance or in his locker.

In a third use case the person with diabetes is going into a canteen. There are context data carriers provided with a barcode on the plates, the barcode indicating the amount of carbohydrates inside the meal. The person scans the barcode. Thereby, in the portable device 3 context dependent control data are generated which are indicating meal bolus based on the bolus calculation for the scanned context data.

The invention claimed is:

1. A control apparatus for providing control data in a medical system, comprising
   a portable device;
   a plurality of active context data carriers, comprising a first context data carrier placed in a first location of a use environment of the portable device, wherein the plurality of active context data carriers provide a local location reference system; and
   a data handling system provided in the portable device, comprising a data input interface, and a device controller functionally connected to the data input interface;
   wherein the data handling system is configured to
   determine a presence of the portable device within the local reference system by determining that the portable device is in vicinity of one or more active context data carriers;
   receive, through the data input interface, first local context data from the first context data carrier, the first local context data being indicative of at least one of location, patient identity, patient activity, and time, wherein the first local context data is received by receiving, by a receiver of the portable device, the first local context data transmitted by a transmitter of the active context data carrier;

generate, in response to receiving the first local context data, context dependent device control data by the device controller, comprising processing of the first local context data and generating the first context dependent device control data in dependence on electronic context information derived from the processing of the first local context data; and output, through a data output interface of the portable device, output data indicative of the first context dependent device control data.

2. Control apparatus according to claim 1, wherein the transmitter of the context data carrier and the receiver of the portable device are configured for contactless data transmission by a transmission technology selected from the following group: near field data communication, and Bluetooth communication.

3. Control apparatus according to claim 1, wherein the portable device comprises a detection module functionally connected to the device controller, the data handling system further configured to detect local vicinity of the portable device to the first context data carrier.

4. Control apparatus according to claim 1, wherein the first context dependent device control data are configured to control at least one process of operation of a medical device selected from the following group: video data output, audio data output, outputting a warning signal, controlling pump operation, and amending at least one of medication plan, a bolus administration, a target range of measurement such as glucose values, a device setting of a medical device such as an insulin pump or a glucose measurement device, a threshold value for measurement values such as glucose values, an insulin profile, and a time block defining a time period.

5. Control apparatus according to claim 1, wherein the portable device is selected from the following group of portable devices: mobile phone, tablet computer, laptop computer, portable medical device, portable medical measurement device, and smart watch.

6. Control apparatus according to claim 1, wherein the plurality of context data carriers comprises a second context data carrier placed in a second location of the use environment of the portable device which is different from the first location, the second local context data carrier providing second context data which are different from the first local context data.

7. The control apparatus according to claim 1, and further including a medical device functionally connected to the control apparatus for receiving context dependent device control data from the control apparatus.

8. The control apparatus according to claim 7, wherein the medical device is selected from the following group of medical devices: blood glucose meter, insulin pump, continuous glucose monitoring system, and insulin pen.

9. A method for controlling a medical system, comprising providing a control apparatus, the control apparatus comprising a portable device, a plurality of active context data carriers with a first context data carrier individually placed in a first location of a use environment of the portable device, wherein the plurality of active context data carriers provide a local location reference system, and a data handling system provided in the portable device and comprising a data input interface, and a device controller functionally connected to the data input interface;

determining a presence of the portable device within the local reference system by determining that the portable device is in vicinity of one or more active context data carriers;

receiving, through the data input interface, first local context data from the first context data carrier, the first local context data being indicative of at least one of location, patient identity, patient activity, and time, wherein the first local context data is received by receiving, by a receiver of the portable device, the first local context data transmitted by a transmitter of the active context data carrier;

generating, in response to receiving the first local context data, context dependent device control data by the device controller, comprising analyzing of the first local context data and generating the first context dependent device control data in dependence on context information derived from the analyzing of the first local context data; and outputting, through a data output interface of the portable device, output data indicative of the first context dependent device control data.

10. Method according to claim 9, wherein the providing the control system comprises loading a software application into a memory of the portable device and running the software application on the portable device.

11. Method according to claim 9, further comprising placing the first context data carrier in a user-defined location of the local use environment of the portable device.

12. A computer program product for controlling a medical system by a control apparatus comprising a portable device, a plurality of active context data carriers with a first context data carrier individually placed in a first location of a use environment of the portable device, wherein the plurality of active context data carriers provide a local location reference system, and a data handling system provided in the portable device and comprising a data input interface, and a device controller functionally connected to the data input interface, the computer program product comprising means for determining a presence of the portable device within the local reference system by determining that the portable device is in vicinity of one or more active context data carriers;

means for receiving, through the data input interface, first local context data from the first context data carrier, the first local context data being indicative of at least one of location, patient identity, patient activity, and time, wherein the first local context data is received by receiving, by a receiver of the portable device, the first local context data transmitted by a transmitter of an active context data carrier;

means for generating, in response to receiving the first local context data, context dependent device control data by the device controller, comprising analyzing of the first local context data and generating the first context dependent device control data in dependence on context information derived from the analyzing of the first local context data; and means for outputting, through a data output interface of the portable device, output data indicative of the first context dependent device control data.

13. Computer program product according to claim 12, wherein the transmitter of the context data carrier and the receiver of the portable device are configured for contactless data transmission by a transmission technology selected from the following group: near field data communication, and Bluetooth communication.

14. Computer program product according to claim 12, wherein the portable device comprises a detection module functionally connected to the device controller, the data handling system further configured to detect local vicinity of the portable device to the first context data carrier.

15. Computer program product according to claim 12, wherein the first context dependent device control data are configured to control at least one process of operation of a medical device selected from the following group: video data output, audio data output, outputting a warning signal, controlling pump operation, and amending at least one of medication plan, a bolus administration, a target range of measurement such as glucose values, a device setting of a medical device such as an insulin pump or a glucose measurement device, a threshold value for measurement values such as glucose values, an insulin profile, and a time block defining a time period.

16. Computer program product according to claim 12, wherein the portable device is selected from the following group of portable devices: mobile phone, tablet computer, laptop computer, portable medical device, portable medical measurement device, and smart watch.

17. Computer program product according to claim 12, wherein the plurality of context data carriers comprises a second context data carrier placed in a second location of the use environment of the portable device which is different from the first location, the second local context data carrier providing second context data which are different from the first local context data.

18. Computer program product according to claim 12, and further including a medical device functionally connected to the control apparatus for receiving context dependent device control data from the control apparatus.

19. Computer program product according to 18, wherein the medical device is selected from the following group of medical devices: blood glucose meter, insulin pump, continuous glucose monitoring system, and insulin pen.

* * * * *